US00PP15161P2

(12) United States Plant Patent
Olesen et al.

(10) Patent No.: US PP15,161 P2
(45) Date of Patent: Sep. 21, 2004

(54) ROSE PLANT NAMED 'POULCS007'

(50) Latin Name: *Rosa hybrida*
Varietal Denomination: POULcs007

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/738,162

(22) Filed: Dec. 16, 2003

(51) Int. Cl.[7] ..... A01H 5/00
(52) U.S. Cl. ..... Plt./149
(58) Field of Search ..... Plt./149

*Primary Examiner*—Anne Marie Grunberg
*Assistant Examiner*—Annette H Para

(57) ABSTRACT

A new garden rose plant of the floribunda class which has abundant, pink flowers and attractive foliage. This new and distinct variety has shown to be uniform and stable in the resulting generations from asexual propagation.

2 Drawing Sheets

Botanical classification: *Rosa hybrida.*
Variety denomination: 'POULcs007'.

SUMMARY OF THE INVENTION

The present invention constitutes a new and distinct variety of garden rose plant which originated from a controlled crossing between an unnamed female parent plant, and a male parent named 'POULskov', described and illustrated in U.S. Plant Pat. No. 9,062 dated Feb. 28, 1995. The two parents were crossed during the summer of 1992 and the resulting seeds were planted in a controlled environment in Fredensborg, Denmark. The new variety is named 'POULcs007'.

The new variety may be distinguished from its unnamed female seed parent, by the following combination of characteristics:

1. While the seed parent has apricot flowers. 'POULcs007' has pink flowers.
2. While the seed parent has 50 to 60 petals. 'POULcs007' has 75 to 80 petals.

The new variety may be distinguished from its male pollen parent, 'POULskov' by the following combination of characteristics:

1. While the pollen parent 'POULskov' has a general tonality of Red Group 49D to Red Group 56D, the same of 'POULcs007' is Red Group 49B.
2. 'POULcs007' develops flower buds in cymes of seven flower buds per stem. 'POULskov' exhibits fewer than seven flowers per stem.

The objective of the hybridization of this rose variety was to create a new and distinct variety for garden use with unique qualities, such as:

1. Uniform and abundant orange-red flowers;
2. Vigorous, but compact growth when propagated both as a budded rose and on its own roots;
3. Disease resistance;
4. Continuous flowering;
5. Suitability for growing in a container.

This combination of qualities is not present in previously available commercial cultivars of this type, known to the inventors, and distinguish 'POULcs007' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULcs007' was selected in the spring 1993 by the inventors as a single plant from the progeny of the aforementioned hybridization.

Asexual reproduction of 'POULcs007' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULcs007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs007'.

Specifically illustrated in SHEET 1:

FIG. 1.1; Open flower, cluster or cyme of open flowers showing branching and the attachment of leaves, buds, and peduncles;

FIG. 1.2; Flower petals, detached;

FIG. 1.3; Sepals, receptacle, and peduncle;

Specifically illustrated in SHEET 2:

FIG. 2.1; Flower bud closed, flower bud as sepals unfold, and partially open;

FIG. 2.2; Leaves showing leaf gloss;

FIG. 2.3; Bare stem exhibiting thorns.

DETAILED DESCRIPTION OF THE VARIETY

The following is a description of 'POULcs007', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'POULmax', a rose variety from the same inventors described and illustrated in U.S. Plant Pat. application Ser. No. 10/192,746 dated Jul. 9, 2002 are compared to 'POULcs007' in Chart 1.

CHART 1

| | 'POULcs007' | 'POULmax' |
|---|---|---|
| General Tonality | Red Group 49B. | Red Group 48C. |
| Receptacle Color | Yellow-Green Group 144B. | Green Group 143C. |
| Petalage | 75 to 80 | 18 to 22 |

Parents:

*Female seed parent.*—Unnamed plant.

*Male pollen parent.*—'POULskov'.

FLOWER AND FLOWER BUD

Blooming habit: Continuous.

Flower bud:

*Bud form.*—Broad based ovoid.

*Sepals.*—Upper Surface: Color: Green Group 143C with intonations of anthocyanine pigments of Greyed-Orange Group 177A. Surface: Moderately pubescent. Lower Surface: Color: Yellow-Green Group 144A with anthocyanic pigments the color of Greyed-Orange Group 176A. Sepal Shape: Sepal apex is cirrhose. Base is flat at union with receptacle. Sepal Margin: Margins have weak foliaceous appendages on three of the five sepals. Moderately pubescent. Size: 25 mm (l)×9 mm (w).

*Receptacle.*—Shape: Funnel shaped. Size: 7 mm (h)× 10 mm (w). Color: Yellow-Green Group 144B.

*Peduncle.*—Surface: Smooth. Length: 50 mm average length. Color: Yellow-Green Group 146C with anthocyanic pigments the color of Greyed-Orange Group 177A. Strength: Strong.

*Borne.*—Singularly to clusters of 7 flower buds per stem.

Flower bloom:

*Fragrance.*—Moderate floral scent.

*Duration.*—The blooms have a duration on the plant of approximately 10 to 12 days. Afterwards, petals fall cleanly away from plant.

*Size.*—Flower diameter is 70 mm when open. Flower depth is 30 mm.

*Form.*—General shape is a rosette with overlapping petals.

Shape of flower when viewed from the side: Upon opening, upper part: Flat. Upon opening, lower part: Flat. Open flower, upper part: Concave. Open flower, lower part: Flattened Convex.

Petalage: Average range is 75 to 80 petals under normal conditions with 10 to 15 petaloids.

Color:

Upon opening, petals:

*Outermost petals.*—Outer side: Marginal Zone is Orange-Red Group 35C to Red Group 38A. Marginal zone coloration blends with Yellow-Orange Group 18D at middle zone. Inner Side: Orange-Red Group 32B with a very light overlay of Red Group 41C.

*Innermost petals.*—Outer side: Orange-Red Group 32B to Red Group 41C at marginal zones. Middle zone is a blend of Yellow-Orange Group 18D and Red Group 41C. Inner Side: Orange-Red Group 32A.

Upon opening, basal petal spots:

*Outermost petals.*—Outer side: Yellow Group 4C. Inner Side: Yellow Group 4B.

*Innermost petals.*—Outer side: Yellow Group 4C. Inner Side: Yellow Group 4A to 4B.

After opening, petals:

*Outermost petals.*—Outer side: Base color of Yellow Group 4D with overlay of Red Group 49C, which is more concentrated at the petal margins. Inner Side: Red Group 49A to 49B.

*Innermost petals.*—Outer side: Base color of Yellow Group 4D with overlay of Red Group 49C, which is more concentrated at the petal margins. Inner Side: Red Group 49A to 49B.

After opening, basal petal spots:

*Outermost petals.*—Outer Side: Yellow Group 4D. Inner Side: Yellow Group 4C.

*Innermost petals.*—Outer Side: Yellow Group 4D. Inner Side: Yellow Group 4C.

General tonality: On open flower Red Group 49B. No change in the general tonality at the end of the $10^{th}$ day. Afterwards, general tonality is Red Group 49C.

Petals:

*Petal reflex.*—Slightly.

*Margin.*—Entire with point in center of margin. Weak undulations of margin observed.

*Shape.*—Apex: Round. Base: Acute.

*Size.*—35 mm (l)×30 mm (w).

*Texture.*—Smooth.

*Thickness.*—Average.

*Arrangement.*—Not Formal.

Petaloids:

*Quantity.*—10 to 15.

*Color.*—Upper Surface: Red Group 38A. Lower Surface: Red Group 38C.

*Size.*—20 mm (l)×11 mm (w).

Reproductive organs:

*Pistils.*—Length: 9 mm. Quantity: 50 (actual count).

*Pollen.*—None Observed.

*Anthers.*—Size: 3 mm. Color: Yellow-Orange Group 18B. Quantity: 107 (actual count).

*Filaments.*—Color: Yellow Group 12C. Length: 10 mm.

*Stigmas.*—Even location to the length of the filaments and the height of the anthers. Color: Yellow-Orange Group 18B with intonations of Red Group 41A.

*Styles.*—Color: Yellow-Green Group 145C.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 60 to 100 cm.

Stems:

*Color.*—Young wood: Green Group 138B. Older wood: Green Group 138A to 138B.

*Surface texture.*—Young wood: Rough with prickles. Older wood: Rough with prickles.

Thorns:

*Incidence.*—25 thorns per 10 cm of stem.

*Size.*—Average length: 6 mm.

*Color.*—Greyed-Orange Group 164B to Greyed-Purple Group 185C.

*Shape.*—Upper: Linear. Lower: Concave.

Plant foliage: Normal number of leaflets on normal leaves in middle of the stem: 5 leaflets.

*Compound leaf size.*—110 mm (l)×70 mm (w).

*Quantity.*—Average.

*Color.*—Mature Foliage: Upper surface is: Yellow-Green Group 147A. Lower surface is: Yellow-Green Group 147C. Juvenile foliage: Upper surface is: Greyed-Purple Group 187B. Lower surface is: Greyed-Purple Group 187B.

Plant leaves and leaflets:

*Stipules.*—Size: 15 mm in length. Apecies extend 5 mm. Shape: Slightly broad based with outward extending apecies. Margins: Finely serrated with stipitate glands present along margin. Margins are entire. Color: Green Group 137C.

*Petiole.*—Length: 35 mm. Anthocyanin: Top side of petiole Greyed-Purple Group 183C. Underneath: Color: Yellow-Green Group 144A. Observations: Prickles observed. Abundant stipitate glands on margins.

*Rachis.*—Length: 30 mm. Above: Color: Greyed-Purple Group 183B. Underneath: Color: Yellow-Green Group 144C. Observations: Many stipitate glands.

*Leaflet.*—Edge: Serrated. Size: 45 mm (L)×28 mm (w). Shape: Generally ovate. Leaflet base is round. Apex is acute. Arrangement: Odd pinnate. Venation: Reticulate. Glossiness: Moderately glossy.

Disease resistance: Above average resistance to mildew, rust, black spot, and Botrytis under normal growing conditions in Jackson County, Oreg.

Cold hardiness: The variety 'POULcs007' has been found to be cold tolerant to USDA Cold Hardiness Zone 6.

We claim:

1. A new and distinct variety of rose plant of the floribunda rose class, substantially as herein illustrated and described as a distinct and novel rose variety due to its abundant pink, disease resistance, and extended period of bloom.

* * * * *

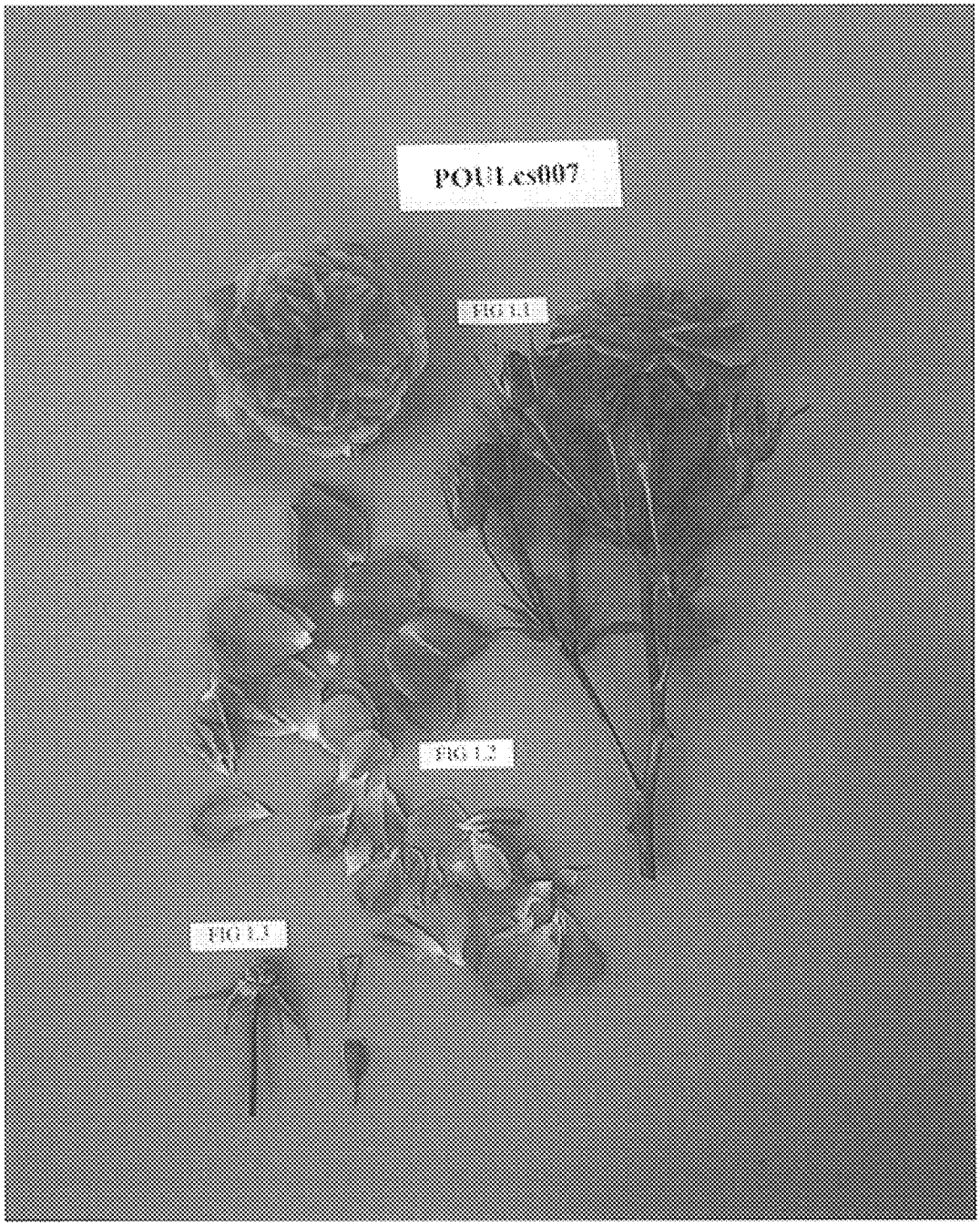
POU1cs007
FIG 1.1
FIG 1.2
FIG 1.3

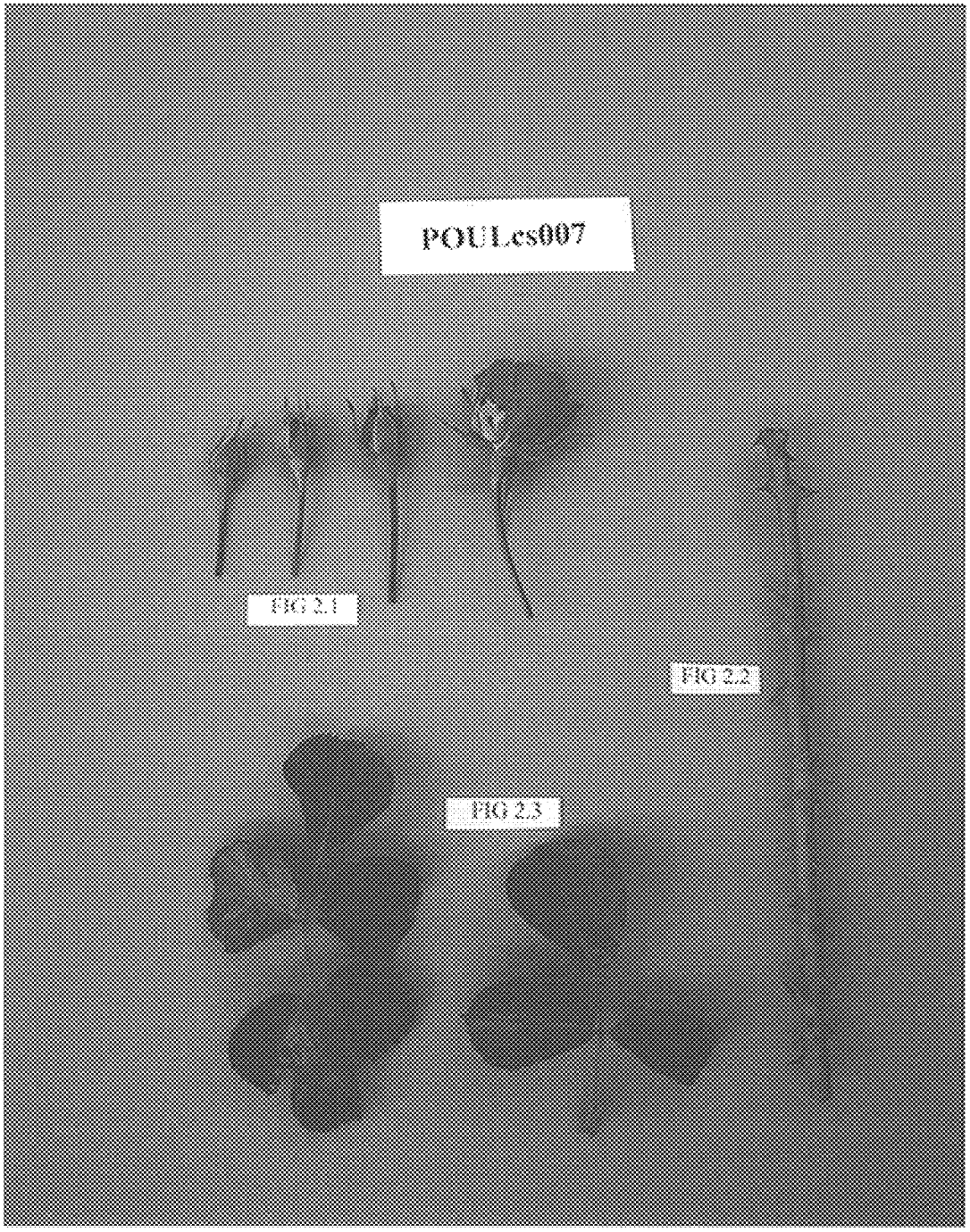
POULcs007
FIG 2.1
FIG 2.2
FIG 2.3